(12) United States Patent
Augustsson et al.

(10) Patent No.: US 11,478,796 B2
(45) Date of Patent: Oct. 25, 2022

(54) METHOD AND SYSTEM FOR OPTICAL OR ELECTRICAL MEASUREMENTS IN DISPERSE FLUIDS

(71) Applicants: ACOUSORT AB, Lund (SE); INSTRUMENTATION LABORATORY COMPANY, Bedford, MA (US)

(72) Inventors: Per Augustsson, Lund (SE); Pelle Daniel Ohlsson, Lund (SE); Ola Jakobsson, Lomma (SE); Klara Andersson, Sjöbo (SE); Gert Blankenstein, Dortmund (DE); Josef Kerimo, Concord, MA (US); Ethan Schonbrun, Auburndale, MA (US)

(73) Assignees: ACOUSORT AB, Lund (SE); INSTRUMENTATION LABORATORY COMPANY, Bedford, MA (US)

( * ) Notice: Subject to any disclaimer, the term of this patent is extended or adjusted under 35 U.S.C. 154(b) by 618 days.

(21) Appl. No.: 16/336,832

(22) PCT Filed: Oct. 9, 2017

(86) PCT No.: PCT/EP2017/075681
§ 371 (c)(1),
(2) Date: Mar. 26, 2019

(87) PCT Pub. No.: WO2018/065626
PCT Pub. Date: Apr. 12, 2018

(65) Prior Publication Data
US 2021/0283607 A1    Sep. 16, 2021

(30) Foreign Application Priority Data

Oct. 7, 2016  (EP) ..................... 16192938
Oct. 7, 2016  (EP) ..................... 16192939

(51) Int. Cl.
*B01L 3/00*      (2006.01)
*G01N 1/40*     (2006.01)
(Continued)

(52) U.S. Cl.
CPC ...... *B01L 3/502761* (2013.01); *G01N 1/4077* (2013.01); *G01N 33/491* (2013.01);
(Continued)

(58) Field of Classification Search
None
See application file for complete search history.

(56) References Cited

U.S. PATENT DOCUMENTS 4,854,170 A     8/1989  Brimhall et al.
5,085,783 A *  2/1992  Feke ................ B01D 21/283
                                                                   210/243
(Continued)

FOREIGN PATENT DOCUMENTS

CN     1200657 A    12/1998
CN     1502068 A    6/2004
(Continued)

OTHER PUBLICATIONS

Brooks, "2.2.2 Acoustic Properties of Crystal Materials" in "Ultrasonic Inspection Technology Development and Search Unit Design", 2012, pp. 35-39.
(Continued)

*Primary Examiner* — Matthew D Krcha
*Assistant Examiner* — Brittany I Fisher
(74) *Attorney, Agent, or Firm* — James S. Keddie; Bozicevic, Field & Francis LLP

(57) ABSTRACT

The invention relates to a method of performing an optical or electrical measurement in a sample of a disperse fluid, the sample comprising particles and a fluid. The method comprises the steps of: a) positioning the sample in a microflu-
(Continued)

Figure 1A:
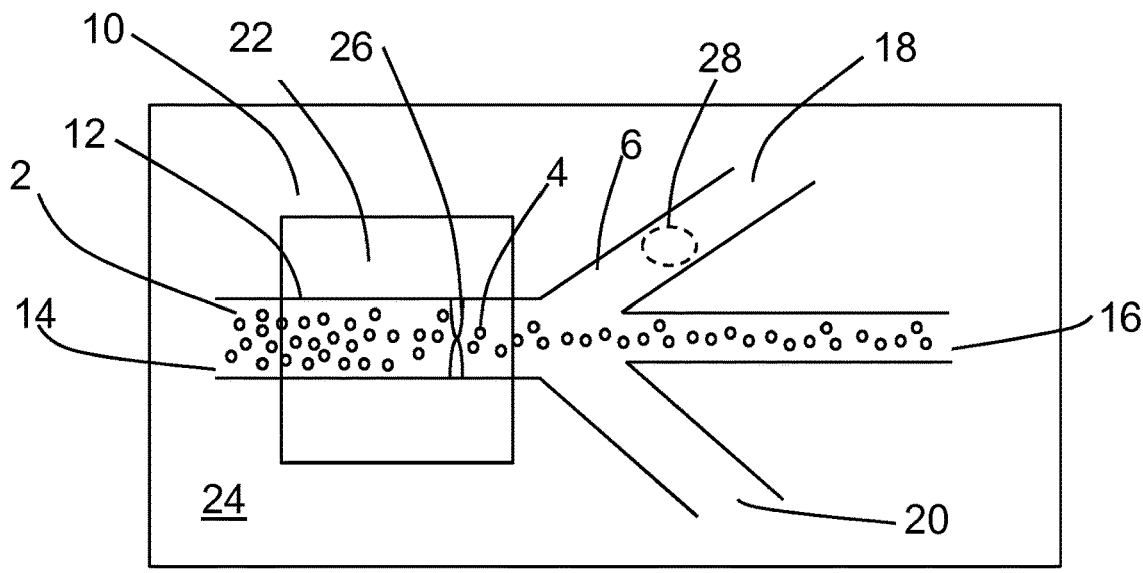

idic cavity having a resonance frequency, b) subjecting the sample, in the cavity, to an acoustic standing wave configured for causing the particles to congregate in at least one first region of the cavity, thereby causing the fluid to occupy at least one second region of the cavity, wherein the frequency of the acoustic standing wave is varied between a frequency below the resonance frequency and a frequency above the resonance frequency, and c) performing an optical or electrical measurement in the fluid in at least one of the at least one second region of the cavity. Varying the frequency ensures reproducible results. The invention also relates to a system therefore and a method and system for measuring hematocrit.

20 Claims, 6 Drawing Sheets

(51) Int. Cl.
  *G01N 33/49* (2006.01)
  *G01N 29/22* (2006.01)
(52) U.S. Cl.
  CPC ............ *B01L 2200/0668* (2013.01); *B01L 2400/0436* (2013.01); *G01N 2001/4094* (2013.01)

(56) References Cited

U.S. PATENT DOCUMENTS

| | | |
|---|---|---|
| 6,597,438 B1 | 7/2003 | Cabuz et al. |
| 2012/0086938 A1* | 4/2012 | Folkenberg ........ G01N 15/1463 356/246 |
| 2014/0011240 A1* | 1/2014 | Lipkens ............... H01L 41/053 435/71.1 |
| 2016/0202237 A1 | 7/2016 | Zeng et al. |

FOREIGN PATENT DOCUMENTS

| | | |
|---|---|---|
| CN | 1906485 A | 1/2007 |
| DE | 102004013960 A1 | 8/2005 |
| EP | 0597577 A1 | 5/1994 |
| WO | WO 97/15229 A1 | 5/1997 |
| WO | WO 2005/054811 A2 | 6/2005 |
| WO | WO 2010/123453 A1 | 10/2010 |
| WO | WO 2011/006525 A1 | 1/2011 |

OTHER PUBLICATIONS

Guhr et al., "Novel sensor combining impedance spectroscopy and surface acoustic waves to detect blood coagulation time and hematocrit value", 2011, IEEE Sensors Proceedings, Limerick, Ireland, Piscataway, NJ.

Lakamper et al., "Direct 2D measurement of time-averaged forces and pressure amplitudes in acousto-phoretic devices using optical trapping", Lab on a Chip, The Royal Society of Chemistry, 2015, 15: 290-300.

Lenshof et al., "Acoustofluidics 8: Applications of acoustophoresis in continuous flow microsystems", Lap on a Chip, The Royal Society of Chemistry, 2012, 12: 1210-1223.

Manneberg et al., "Flow-free transport of cells in microchannels by frequency-modulated ultrasound", Lap on a Chip, The Royal Society of Chemistry, 2009, 9: 833-837.

Seo et al., "Ultrasonic flow-through filtration of microparticles in a microfluidic channel using frequency sweep technique", Journal of Mechanical Science and Technology, 2013, 27(3): 825-830.

* cited by examiner

METHOD AND SYSTEM FOR OPTICAL OR ELECTRICAL MEASUREMENTS IN DISPERSE FLUIDS

CROSS-REFERENCE TO RELATED APPLICATIONS

This application is a § 371 national phase of International Application No. PCT/EP2017/075681, filed on Oct. 9, 2017, which claims the benefit of European Patent Application No. 16192938.5, filed on Oct. 7, 2016, and European Patent Application No. 16192939.3, filed on Oct. 7, 2016, which applications are incorporated by reference herein.

TECHNICAL FIELD OF THE INVENTION

The present invention relates generally to the field of methods and systems for optical or electrical measurements in disperse fluids. Further the present invention relates specifically to the field of absorbance measurements in biological fluids where the absorbance is measured in a part of the fluid devoid of particles and/or cells.

BACKGROUND OF THE INVENTION

Disperse fluids are made up of particles dispersed in one or more continuous phases, e.g. fluids. One disperse fluid of special interest is blood which is made up of about 45% red blood cells or erythrocytes, about 0.7% white blood cells or leukocytes, and the remaining about 54.3% being blood plasma, however, these values may vary between individuals and these values may also vary greatly in some diseases where the volume fraction of red blood cells may be from 25-60% of the volume of the blood.

Optical or electrical measurements performed on blood sample include absorbance measurements for the determination of the concentration of free hemoglobin in a blood sample, this measurement being an indication on the amount of red blood cells that have ruptured thus releasing hemoglobin into the blood plasma. The degree of hemolysis, i.e. the amount of red blood cells that have ruptured, is an important diagnostic parameter for directly assessing the health of a patient. It is further of interest as hemolysis, and the corresponding release of the contents of the red blood cells into the blood plasma, will affect the results of other measurements performed on the blood sample.

Typically blood samples are analyzed using blood gas analysis wherein the partial pressures of oxygen and carbon dioxide, as well as a number of other parameters of the sample such as pH, $HCO_3^-$, p50, $sO_2$, base excess, ctHb, COHb, MetHb, $Ca^{2+}$ and $K^+$, are determined. At least eight of these commonly measured parameters are affected by returning lower values for pH, $pO_2$, $pO_2$, COHb and $Ca^{2+}$, and by returning higher values for $pCO_2$, $HCO_3^-$ and $K^+$, when compared to the values obtained from a non-hemolysed blood sample.

The amount of free hemoglobin may be determined by absorbance measurements in a cell free portion of the blood. This cell free portion is created by having the red and white blood cells sediment, either spontaneously under the force of gravity or in a centrifuge, so that the blood sample is divided up into a first portion comprising clear blood plasma and a second portion comprising the blood cells.

These methods however have drawbacks in that they require significant amounts of time (spontaneous settling) or require costly equipment (centrifuge) and are not practical to integrate in automated systems handling small amounts of blood.

DE102004013960 proposes a method of determining the degree of hemolysis in a sterile container, i.e. a blood bag, in which ultrasound is to be used to create or expedite sedimentation of blood cells in the tubing connected to the blood bag, thus aiming at forming an optically clear area of blood plasma for determining the concentration of hemoglobin optically. As no working examples are provided it remains in doubt whether ultrasound could in fact be used as proposed—in particular the present inventors have realized that due to the non-standardized dimensions of the blood bag and the tubing it would be doubtful whether the blood cells could be separated from the blood plasma as proposed. Further that approach is not suitable for small volume samples from blood draw or finger pricks.

US 2016/202237 A1 discloses a device and method for analyte detection and analytes in a particulate bearing fluid such as whole blood having an instrument, such as an acoustic transducer, for partitioning the particles from the fluid that is integrated with a detector for analyses of one or more particulate bearing fluid analytes while the particles in the particulate bearing fluid are partitioned.

Andreas Lenshof et al: "Acoustofluidics 8: Applications of acoustophoresis in continuous flow microsystems", LAB ON A CHIP, vol. 12, no. 7, 7 Mar. 2012, discloses applications of Acoustophoresis in continuous flow microsystems.

U.S. Pat. No. 4,854,170 A discloses an ultrasound apparatus for determining hematocrit using a sample of blood placed in a microhematocrit capillary tube and coupling this tube to an ultrasound transducer operated at a certain frequency to pack red blood cells into bands, the thickness of which, in relation to the thickness of bands of the remaining plasma, being an indication of the hematocrit of the blood cells.

Dae-Cheol Seo et al: "Ultrasonix flow-through filtration of microparticles in a microfluidic channel using frequency sweep technique" Journal of mechanical Science and technology vol. 27, no. 3, 1 Mar. 2013) discloses flow-through particle filtration using frequency varying ultrasound, the frequency sweep of the ultrasonic standing wave translocating particles across a microchannel for filtrating out the particles without barriers.

Mark V. Brooks: "2.2.2 Acoustic Properties of Crystal Materials" In: "Ultrasonic Inspection Technology Development and Search Unit Design" 1 Jan. 2012, John Wiley & Sons, discloses average acoustic Characteristics of some materials.

OBJECT OF THE INVENTION

The present invention aims at obviating the aforementioned disadvantages and failings of previously known methods for optical or electrical measurements in disperse fluid such as blood, in particular the disadvantages accompanied by using gravitational force or centrifugation in obtaining a clear portion for the measurements.

A primary object of the present invention is therefore to provide a method of performing optical or electrical measurements in disperse fluids.

It is another object of the present invention to provide a microfluidic system for performing optical or electrical measurements in disperse fluids.

SUMMARY OF THE INVENTION

At least one of the abovementioned objects or at least one of the further objects which will become evident from the below description, are according to a first aspect of the present invention achieved by a method of performing an optical or electrical measurement in a sample of a disperse fluid, the sample comprising particles and a fluid, comprising the steps of:

a) positioning the sample in a microfluidic cavity having a resonance frequency, b) subjecting the sample, in the cavity, to an acoustic standing wave configured for causing the particles to congregate in at least one first region of the cavity, thereby causing the fluid to occupy at least one second region of the cavity, wherein the frequency of the acoustic standing wave is repeatedly varied between a frequency below the resonance frequency and a frequency above the resonance frequency, and c) performing an optical or electrical measurement in the fluid in at least one of the at least one second region of the cavity.

Thus the present invention is based on the discovery by the present inventors that, while it is generally a need for very high precision formed microfluidic cavities and proper fine tuning of the frequency of the acoustic standing wave in order to obtain a proper congregation or partitioning of particles, by repeatedly varying the frequency as defined in the method according to the first aspect of the present invention these requirements may to a large extent be dispensed with. Thus, by varying the frequency between a frequency below the resonance frequency and a frequency above the resonance frequency a more stable congregation of the particles in the at least one first region of the cavity is achieved. This was unexpected and represents significant progress compared to earlier experiments at a single frequency where small irregularities in the microfluidic cavity or slight mistuning of the frequency of the acoustic standing wave resulted in insufficient congregation/partitioning. Furthermore, it is surprising that despite varying the frequency, which could be expected to render the congregation or partitioning of the particles less effective since actuation at the optimal frequency could only be performed a small fraction of the time, fast and reproducible congregation of the particles, was achieved. The method according to the first aspect of the present invention is therefore useful because it provides an efficient congregation of the particles even where the substrate with cavity is manufactured with larger tolerances, and hence varying resonance frequencies, between individual substrates, thus providing for using cheap disposable substrates. This makes it easier and cheaper to implement point of care optical or electrical measurements in disperse fluid and does not require time consuming centrifugation. This approach dispenses with the otherwise necessary per chip/substrate and per measurement calibration routines or visual or other surveillance of the congregation of the particles during operation because it compensates for the speed of sound being dependent on the type of sample. This further results in that the at least one second region, when the sample is subjected to the acoustic standing wave, is formed in a more predictable and reproducible location relative to the cavity. This makes it easier to perform the optical or electrical measurement, further it allows for arranging the detector so it is directed towards one of the at least one second regions prior to subjecting the sample to the acoustic standing wave. This makes it possible to use a simple detector, such as for example a single light source and a single photo detector or photodiode, or a simple electrode, also when the substrate is manufactured with larger tolerances as the second region in which the optical or electrical measurements is to be performed may be expected to form in approximately the same position relative to the dimensions of the cavity each time, which is often not the case when actuation is performed at a single frequency.

Optical measurements include absorbance measurements, fluorescence measurements, Raman spectroscopy, chemiluminescence and scattering. Electrical measurements include electrical impedance (spectroscopy) measurements, electrochemical measurements, voltammetry, conductivity.

Preferably the optical or electrical measurements is an absorbance measurement. Absorbance measurement may comprise measurements of optical absorbance, measurements of optical transmission, measurements of absorbance at one or more wavelengths, measurements of transmission at one or more wavelengths.

The sample should be in fluid form and in a viscosity suitable for it being positioned in the cavity.

The disperse fluid may for example comprise undiluted or diluted whole blood, intracellular fluid, interstitial fluid, synovial fluid, peritoneal fluid, urine, yeast cell cultures, bone marrow, stroma, dissociated cells from normal or cancerous tissue, milk.

The particles may comprise red blood cells, white blood cells, platelets, cancer cells, bacterial cells, viruses, yeast cells, dust particles, silica particles and polymer particles.

The fluid may be plasma, water, urine, yeast cell broth, cell culture medium, saline solutions, phosphate buffered saline, intracellular fluid or interstitial fluid, milk plasma.

Some embodiments of the method according to the first aspect of the present invention may comprise further steps of adding other molecular components, such as reagents, pH modifiers (acids, bases) to the disperse fluid for mixing with the disperse fluid before the disperse fluid is positioned in the cavity to in order to affect the optical properties of the fluid.

The sample may be positioned in the cavity by pumping, by pressure, by suction, by the action of electrical fields, by gravity, and by capillary action.

The microfluidic cavity may be closed to the environment. The microfluidic cavity is preferably a channel having a square or rectangular cross section. The microfluidic cavity may for example have a cross sectional width of 1 to 100 such as 1 to 20 times the cross sectional height. In this case the length of the microfluidic cavity is at least the same as the width. The width may for example be from 0.3 mm to 5 mm. The height may for example be from 0.025 mm to 1 mm.

Resonance frequencies of the microfluidic cavity are dependent on the dimensions because, in order for a standing wave to form the wavelength $\lambda$ of the wave, which wavelength is inversely proportional to the frequency, must be $n\lambda/2$ where n is a positive integer.

The following are the first 3 resonances for a standing wave directed along the width dimension of the cavity:

a first resonance frequency f is associated with an acoustic standing wave $\lambda/2$ corresponding to a first harmonics w here the pressure anti nodes of the standing wave are positioned near the walls of the cavity and a single pressure node is formed in the middle of the cavity, thus causing the particles to congregate in the center of the cavity, this being the first region and the regions near the side walls of the cavity being the second regions. Thus we get: wall 1-fluid 1-particles 1-fluid 2-wall 2.

In a second harmonics, corresponding to a resonance frequency that is two times the first resonance frequency, i.e. $2f$, a standing wave $\lambda$ is formed having two nodes and three antinodes, thus generally forcing the particles to congregate in two bands on both sides of the center of the cavity, this being the first regions and the center and sides of the cavity being the second regions. Thus we get: wall 1-fluid 1-particles 1-fluid 2-particles 2-fluid 3-wall 2. This is the preferred resonance frequency.

A third resonance frequency, corresponding to a third harmonics, is three times the first resonance frequency, i.e. $3f$, and is associated with a standing wave $3\lambda/2$ having 3 nodes and four antinodes, thus forcing the particles to congregate in three positions in the cavity, these three being the first regions, these positions being spaced apart from each other and from the walls of the cavity to form three second regions. Thus we get: wall 1-fluid 1-particles 1-fluid 2-particles 2-fluid 3-particles 3-fluid 4-wall 2.

Accordingly the term resonance frequency is to be understood to comprise any frequency in which a standing wave may form in the cavity, and a frequency causing the formation of a standing wave is considered a frequency configured for causing the particles to congregate in at least one first region. Additionally it should be mentioned that even if the resonance, and thus the standing wave, is predominantly in a width dimensions, there will always be components of resonance along the length dimension of the cavity and potentially also in the height direction. These three-dimensional resonances result in several resonance frequencies close to the one-dimensional resonance frequency, each with an associated focusing pattern. Sweeping the actuation frequency over several of these resonance frequencies makes it possible to take advantage of all of them and create a more predictable and even acoustic focusing, generated by the resulting weighted average of the acoustic fields for the separate resonances and thus combined focusing patterns.

The understanding that the acoustic resonances have to be understood in three dimensions and not only simplified to one dimension thus generates practically crucial effects, by generating a predictable, repeatable and robust acoustic focusing pattern and congregation of the particles. This in turn enables detection at predictable, repeatable positions in the system, not possible with single frequency actuation.

The resonance frequency of the cavity, and thus the frequency of the acoustic standing wave, may thus be from 0.15 MHz to 10 MHz.

The frequency may be varied from a frequency 20% below the resonance frequency to a frequency 20% above the resonance frequency. Preferably the frequency is varied from a frequency 10% below the resonance frequency to a frequency 10% above the resonance frequency. The frequency may be varied continuously, or alternatively only during some time, during the time that the sample/disperse fluid is subjected to the acoustic standing wave. The frequency may be varied linearly, or logarithmically.

The frequency should not be varied from a frequency that is so low, or to a frequency that is so high, that the frequency corresponds to a different resonance frequency of the cavity that will lead to a different number of nodes and antinodes than what is obtained at the resonance frequency.

In other words the frequency $f_{DN}$, for causing the particles to congregate in at least one first region of a cavity having some dimension D corresponding to N half wavelengths of the acoustic standing wave corresponding to $f_{DN}$, should, when varied according the aspects of the present invention, always be higher than $(c*(N-1))/(2*D)$ and lower than $(c*(N+1))/(2D)$, where c is the speed of sound in the fluid.

In practice a sweep range of 1% to 40% of $f_{DN}$, i.e. the frequency being varied over the range of $\pm 0.5$-20% of $f_{DN}$, is sufficient to cover the resonance frequencies corresponding to a certain number of pressure nodes as well as the fabrication tolerances of the channel and the variation in sample speed of sound.

The actuation signal for the ultrasound transducer may preferably be a linearly chirped sine with a repetition rate of 1000 Hz, and amplitude of approximately 15 Vpp (Voltage peak-peak).

In other words the actuation signal for the ultrasound transducer may for example be a linearly chirped sine with a sweep time of 1 ms. The amplitude for the signal may be 15 Vpp (Voltage peak-peak)

The sweep time should be much shorter than the time frame during which congregation occurs. Thus the repetition rate should be high enough so that the sweep time is much shorter than the time frame during which congregation occurs As an example, when the particles are congregated in the cavity over a time frame of 5 seconds the repetition rate of the sweep can be set such that the frequencies are cycled through 100 times or more, i.e. at least 20 repetitions per second corresponding to a sweep time of 50 ms or less.

Thus the sweep time may for example be 100 ns-50 ms, such as 1 ms to 50 ms. Too slow sweep time leads to the shape of the first and second regions changing during the measurement time, i.e. the time that the sample is subjected to the acoustic standing wave.

The concept of sweeping the actuation frequency is not specific for resonant cavities, but also applicable to standing waves generated e.g. by surface acoustic waves or other resonances in the system. Here it has the same function of compensating for variations in sample acoustic properties or temperature, compensating for variations in system dimensions due to e.g. fabrication tolerances and temperature expansion and utilizing several standing waves to generate a more even and predictable focusing pattern.

The optical or electrical measurement is preferably only performed in one of the second regions for simplicity, however it is also feasible to perform the optical or electrical measurement in all of the second regions to increase accuracy and robustness of the method. In the case of an absorbance measurement absorbance or transmission images can be acquired of the whole cavity and all clarified regions, i.e. second regions, can be analyzed with appropriate image analysis algorithms.

In a preferred embodiment of the method according to the first aspect of the present invention the acoustic standing wave is configured for causing in particles to congregate in one or two first regions of the cavity. This is advantageous as it results in large second regions to perform the optical or electrical measurement in, thus increasing the probability that the measurement is not affected by the particles. This corresponds to a frequency associated with a wavelength of the acoustic standing wave that is the same or of the relevant dimension, typically width, of the cavity.

In an alternative embodiment of the method according to the first aspect of the present invention the acoustic standing wave, and/or the cavity, is configured for causing the particles to congregate in more than two first regions of the cavity. This may be advantageous as it provides further second regions in which to perform the optical or electrical measurement. The frequency may be configured by increasing it to four times the first resonance frequency or even further. The cavity may be configured by increasing the dimensions of the cavity.

In the preferred embodiment of the method according to the first aspect of the present invention the method further comprises the step of:

d) generating a flow of the sample through the cavity. This is advantageous as it allows the method to be used for inline and online optical or electrical measurements.

The flow may be generated by pumping, by pressure, by suction, by the action of electrical fields, by gravity, and by capillary action.

The cavity may be fluidly connected to an inlet, through which the sample is introduced into the cavity, and fluidly connected to an outlet, through which the sample leaves the cavity. More than one outlet may be fluidly connected to the cavity in order to lead of different part of the sample to different outlets.

In the preferred embodiment of the method according to the first aspect of the present invention the cavity is elongated and fluidly connected at one end to an inlet and at another opposite end to an outlet. This is advantageous as it allows the use of simple glass capillaries for providing the cavity. Typically the length of the cavity should be at least 5 times its width. In some embodiments the transverse dimension of the cavity is larger than the transverse dimensions of an inlet and an outlet to the cavity.

In the preferred embodiment of the method according to the first aspect of the present invention the cavity is formed in a substrate. The substrate may be made of silicon but may be made of polymeric material such as plastic, or alternatively glass. Also other materials such as ceramics and metals are possible. These materials are cheap and therefore suitable for performing the optical or electrical measurements in the field on in a point of care setting, as disposable consumables.

The substrate may be planar, such as a chip, or alternatively the substrate may be formed as a capillary.

In the preferred embodiment of the method according to the first aspect of the present invention ultrasound energy, for causing the acoustic standing wave is transferred to the substrate from at least one ultrasound transducer solely via a glass coupling member connected to the ultrasound transducer and the substrate. This is advantageous as it makes it easier to access the cavity for performing in particular optical measurements. The glass coupling member may be connected to the ultrasound transducer and the substrate by adhesives, or by being positioned so that they contact each other.

In the preferred embodiment of the method according to the first aspect of the present invention the sample is a whole blood sample whereby the particles comprises at least red blood cells and the fluid comprises at least blood plasma. The particles may further comprise white blood cells.

In the preferred embodiment of the method according to the first aspect of the present invention the optical or electrical measurement is an absorbance measurement comprising determining the amount or concentration of free hemoglobin in the blood plasma. The amount or concentration of free hemoglobin is related to the degree of hemolysis, i.e. the percentage of the red blood cells in the sample that have lysed and released inter alia hemoglobin. Based on the result of the absorbance measurement, which result inter alia may be an absorbance value or a transmission value, the corresponding amount or concentration of free hemoglobin may for example be determined through comparing this value with values obtained from measurement of reference samples with known degrees of hemolysis.

In one embodiment of the method according to the first aspect of the invention the method, where the sample is a whole blood sample and/or where the absorbance measurement comprises determining the amount or concentration of free hemoglobin in the blood plasma, the method further comprises the steps of:

d) determining a relationship between the volume of the red blood cells in the at least one first regions and the volume of the blood plasma in the at least one second regions, and e)

determining the hematocrit of the blood sample based on the relationship.

The determining of the relationship and the determining of the hematocrit is to be performed as discussed in relation to the third and fourth aspects of the present invention described further below.

Thus the determining of the relationship may be made by measuring the volume of the at least one first region and the volume of the at least one second region.

The combined volume of all first regions and the combined volume of all second regions may be measured for determining the relationship.

The relationship of the volumes may be determined by measuring the area of the at least one first region and the area of the at least one second region, the areas being determined in a plane made up of two orthogonal dimensions (XY, length-width) of the cavity provided that the regions have the same extension in the third dimension (Z, height) of the cavity, or that the measurement is adjusted for the variation in depth.

At least one of the abovementioned objects, or at least one of the further objects which will become evident from the below description, are according to a second aspect of the present invention achieved by a microfluidic system for performing an optical or electrical measurement in a sample of a disperse fluid, the sample comprising particles and a fluid, the system comprising a substrate with a microfluidic cavity formed in the substrate, the microfluidic cavity having an inlet for allowing the sample into the microfluidic cavity, an ultrasound transducer connectable to the substrate for generating an acoustic standing wave in the microfluidic cavity, a drive circuit connectable to the ultrasound transducer and configured to drive the ultrasound transducer with a frequency which is repeatedly varied between a frequency below a resonance frequency of the microfluidic cavity and a frequency above the resonance frequency so as to cause the particles to congregate in at least one first region of the cavity, thereby causing the fluid to occupy at least one second region of the cavity, and a detector arranged for performing an optical or electrical measurement in the fluid in at least one of the at least one second region of the cavity.

As discussed above for the method according to the first aspect of the present invention, by the varying of the frequency of the ultrasound transducer a more stable congregation of the particles in the at least one first region of the cavity is achieved.

The microfluidic system may further comprise a container for storing the sample, a pump or other device for causing the sample to enter the cavity, a temperature control device for heating or cooling the substrate as needed, and a receptacle for receiving the sample once the optical or electrical measurement has been performed.

As above the substrate may be made of silicon, polymers such as plastic, or glass.

As above the microfluidic cavity is preferably elongated.

The ultrasound transducer is preferably a piezoelectric actuator. The ultrasound transducer may be connected to the substrate. The acoustic standing wave is generated by the vibrations in the ultrasound transducer being transferred to the substrate and causing the walls of the cavity to vibrate.

The drive circuit may comprise a function generator electrically connected to the ultrasound transducer. The drive circuit is configured, by comprising a function generator, to drive the ultrasound transducer with a frequency that varies. As above the frequency may be varied in several ways.

The detector may be arranged to perform the optical or electrical measurement in a single point only. In the case of the detector being an optical detector it may comprise a light source and a single detector or sensor for detecting light from the light source, or alternatively the sensor may detect the light from the light source in a plurality of spatial positions relative to the cavity. The detector or sensor may thus comprise a plurality of light sensitive diodes, camera, a CCD, a CMOS, or similar. The optical detector may comprise a single light source or a plurality of light sources, each of which may emit light at a single, at a finite number of wavelengths, or as a continuous spectrum. Preferably the light source emits light at one or a finite number of wavelengths. An electrical detector may comprise electrodes provided in the cavity.

In the preferred embodiment of the system according to the second aspect of the present invention the system further comprises a housing comprising a receptacle arranged to receive at least part of the substrate,
  wherein the ultrasound transducer is provided in the housing and is arranged to connect to the substrate when the substrate is received in the receptacle, and
  wherein the detector is provided in the housing and is arranged in a predetermined position relative to the substrate when the substrate is received in the receptacle,
    the predetermined position being arranged for allowing the detector to perform the optical or electrical measurement in the at least one of the at least one second region of the cavity.

This is advantageous as it provides for using a simple detector since the relative positions of the substrate with cavity and the housing with detector may be arranged so the detector is able to perform the optical or electrical measurement in at least one of the second regions. The position of the one or more second regions relative to the substrate can be determined based on the dimensions of the cavity and the position of the cavity on the substrate, and further based on which harmonic, i.e. which of the first, second, third, etc. resonance frequency of the cavity that the frequency of the acoustic standing wave is varied about. As the varying of the frequency ensures that a stable and reproducible congregation of the particles is achieved, a suitable second region for the optical or electrical measurement can be predicted and the detector positioned accordingly.

The housing may comprise a handheld housing for a field or point-of-care optical or electrical measurement.

The receptacle may be provided inside the housing or on the surface of the housing. At least a part of the substrate should be received in the receptacle so that the substrate may be held in position relative to the housing.

In order for the ultrasound transducer to be able to generate the acoustic standing wave in the cavity it must connect to the substrate. This connection may be established by physical contact.

In the preferred embodiment of the system according to the second aspect of the present invention the system further comprises a glass coupling member attached to the ultrasound transducer for connecting the ultrasound transducer to the substrate. This is advantageous as it allows for positioning the ultrasound transducer separate from the substrate, thus making it easier to arrange optical detectors for obtaining access to the second regions.

In some embodiments of the system according to the second aspect of the present invention the cavity is elongated and fluidly connected at one end to an inlet and at another opposite end to an outlet, as described above.

In some embodiments of the system according to the second aspect of the present invention the detector is further arranged for determining a relationship between the volume of the particles in the at least one first regions and the volume of the fluid in the at least one second regions.

The detector may be arranged as discussed in relation to the third and fourth aspects of the present invention described further below. Alternatively the system may comprise a first detector for optical or electrical measurements, and a second detector for determining the relationship.

The detector may be configured to determine the relationship by being configured to measure the volume of the at least one first region and the volume of the at least one second region.

As above the volume of all regions may be measured, and alternatively the relationship can be determined from the areas of the regions.

Further advantages with and features of the invention will be apparent from the other dependent claims as well as from the following detailed description of preferred embodiments.

BRIEF DESCRIPTION OF THE DRAWINGS AND DETAILED DESCRIPTION

A more complete understanding of the abovementioned and other features and advantages of the present invention will be apparent from the following detailed description of preferred embodiments in conjunction with the appended drawings, wherein:

FIG. 1 is a schematic view from above of a first embodiment of the method and system according to the first and second aspect of the present invention, FIG. 2 is photographs showing the congregation of red blood cells with and without varying the frequency of the acoustic standing wave.

Figure 3:
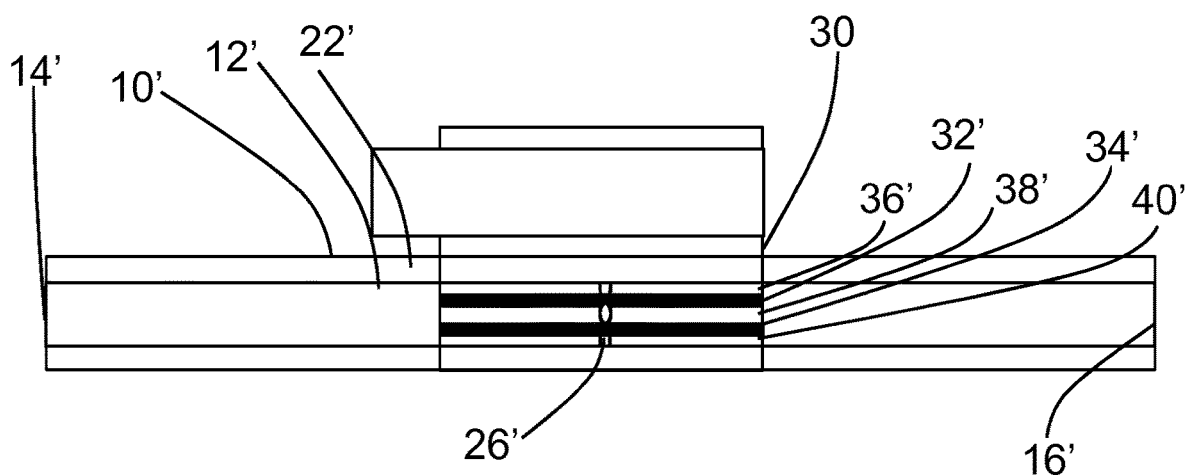
Figure 4A:
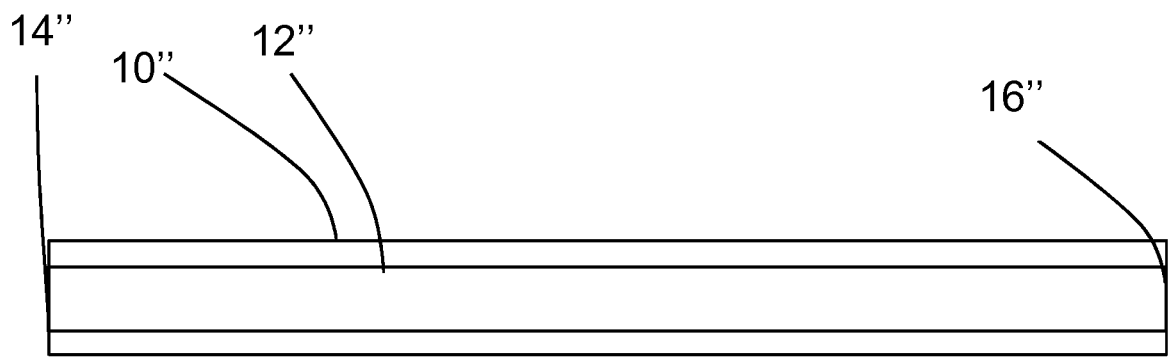
Figure 4A:
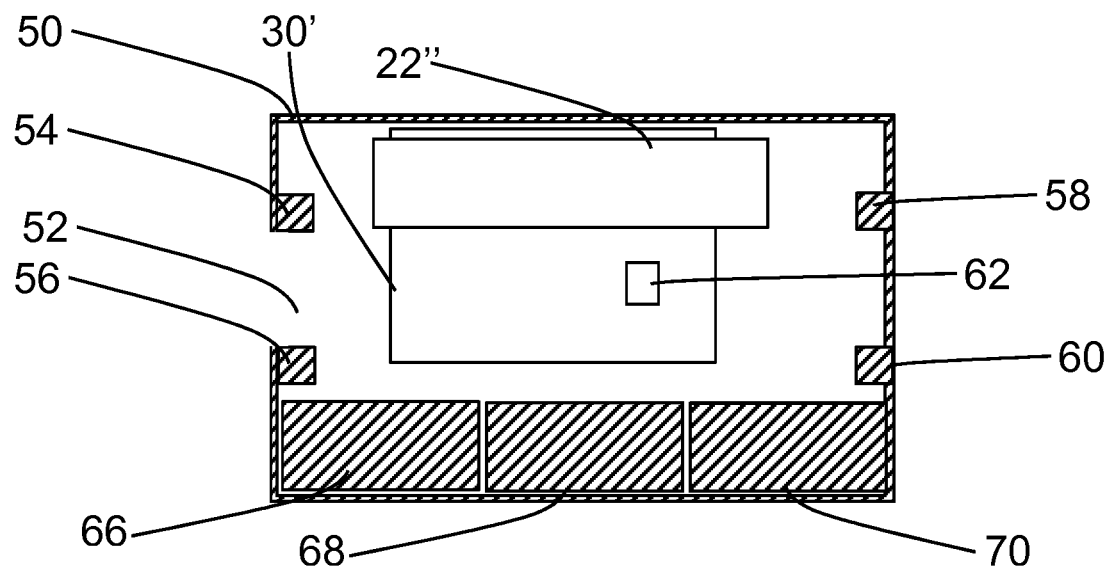
Figure 4B:
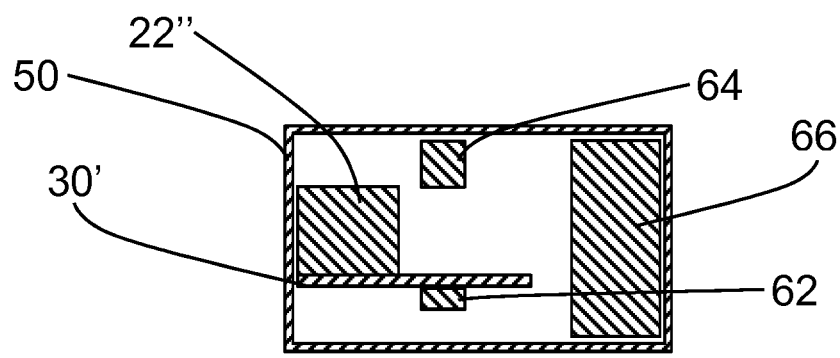
Figure 5A:
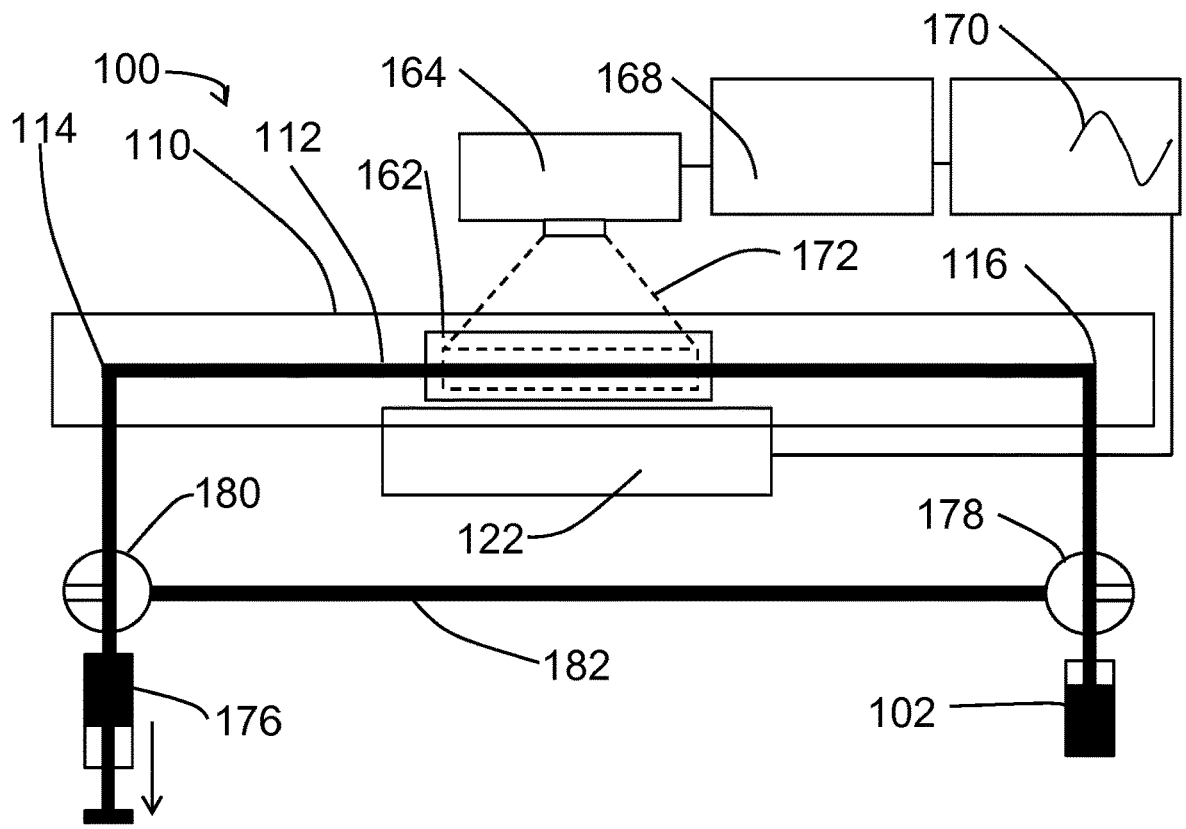
Figure 5B:
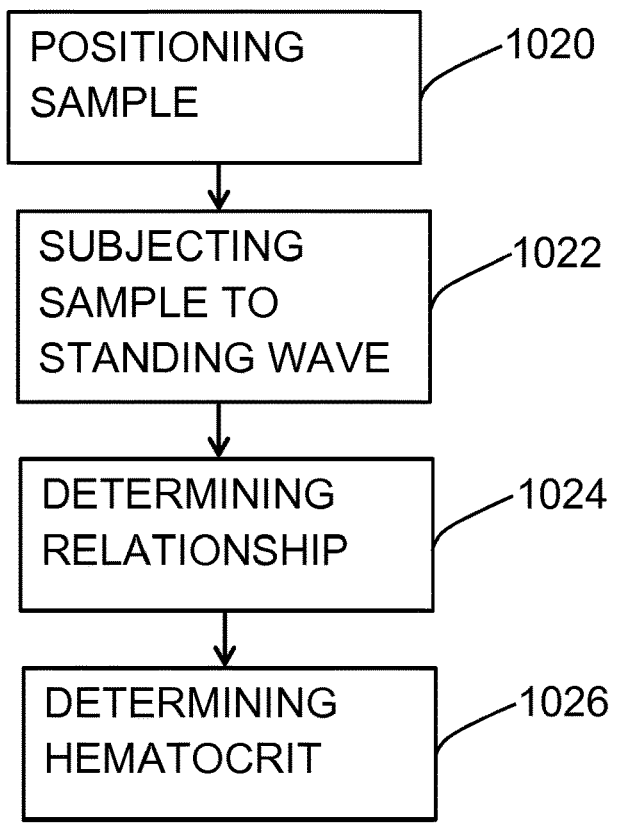
Figure 6:
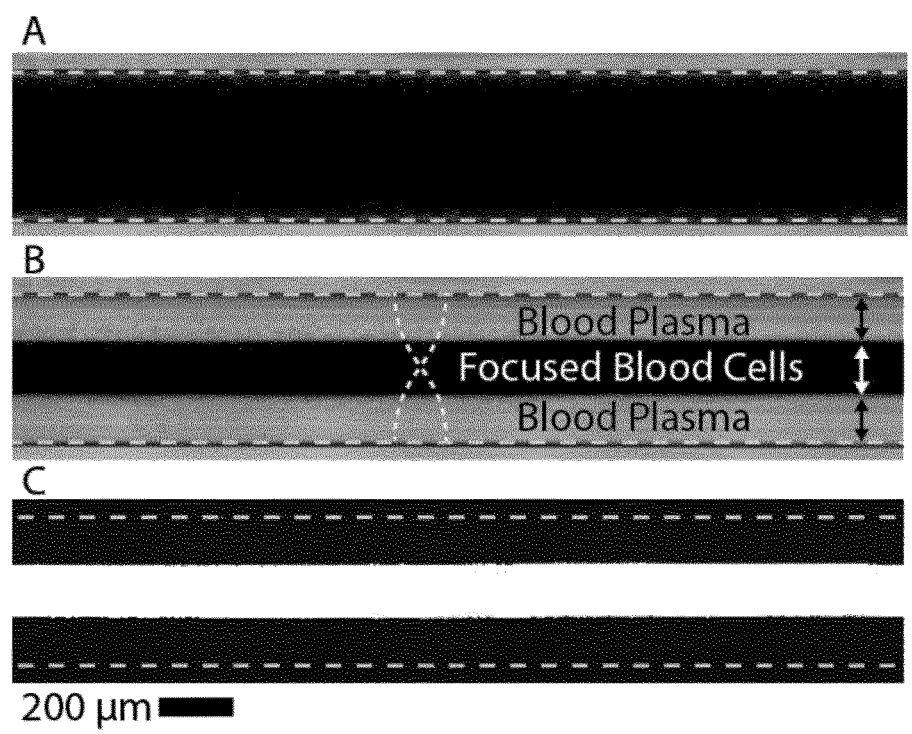
Figure 7:
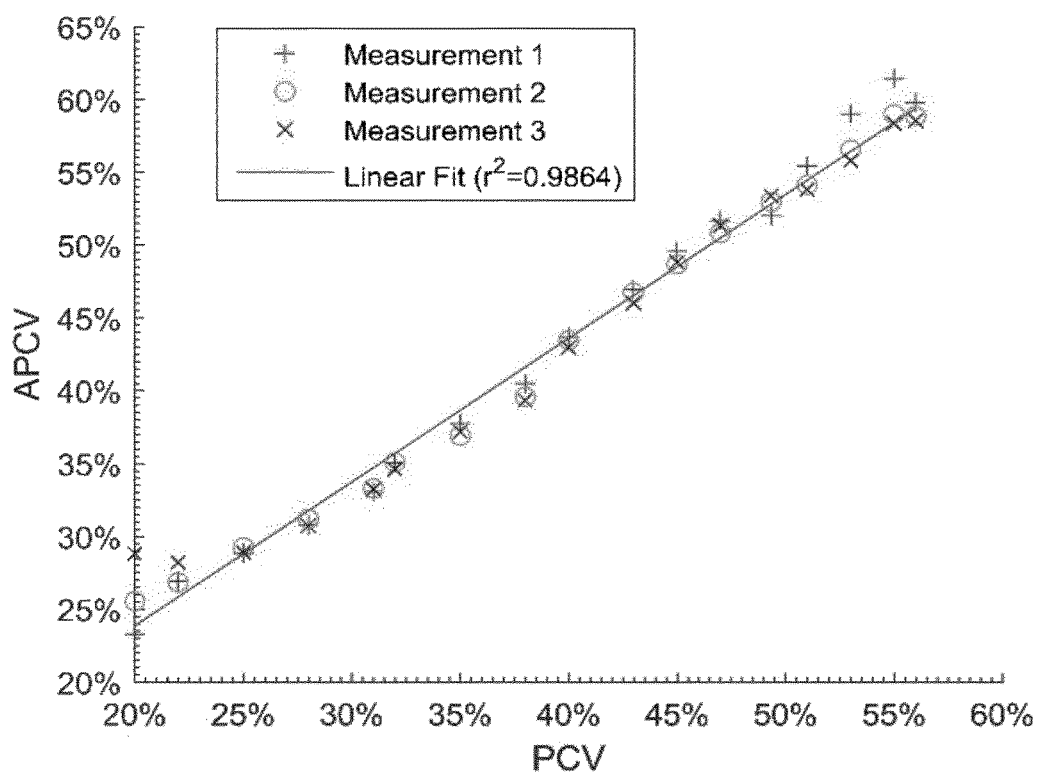
Figure 8:
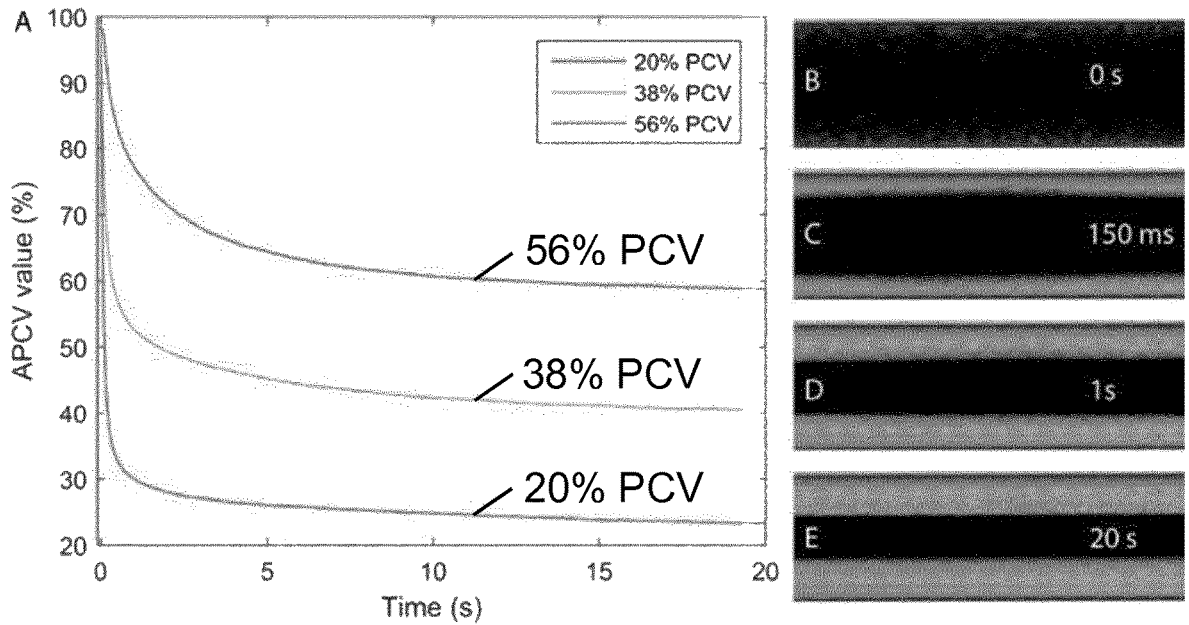
Figure 9:
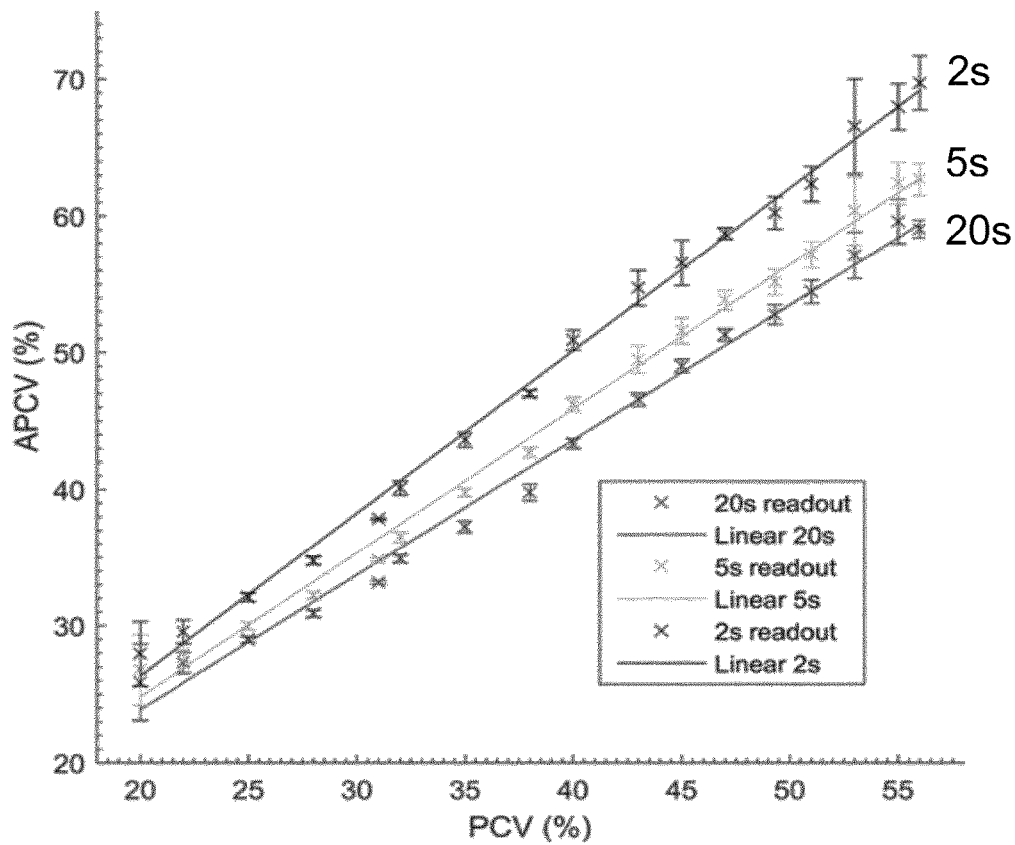

FIG. 3 is a schematic view from above of a second embodiment of the method according to the first aspect of the present invention, FIG. 4 is a schematic part cross sectional view of a first embodiment of a system according to the second aspect of the present invention, FIG. 5 is a schematic view of an embodiment of the method according to the third aspect of the present invention being performed using a first embodiment of the system according to the fourth aspect of the present invention, FIG. 6 shows photographs of the microfluidic cavity and subsequent thresholding techniques used to determine the area occupied by red blood cells vs the area occupied by blood plasma, FIG. 7 is a graph showing the correlation between the Acoustically Packed Cell Volume (APCV) and the Packed Cell Volume (PCV), FIG. 8 shows the temporal evolution of the relationship between the area occupied by red blood cells vs the are occupied by blood plasma, and FIG. 9 is a graph showing the correlation between APCV and PCV obtained at different time points.

In the figures and the description the same reference numeral is used to refer to the same feature. A ' added to a reference numeral indicates that the feature so referenced has a similar function, structure or significance as the feature carrying the reference numeral without the ', however not being identical with this feature.

Figure 1B:
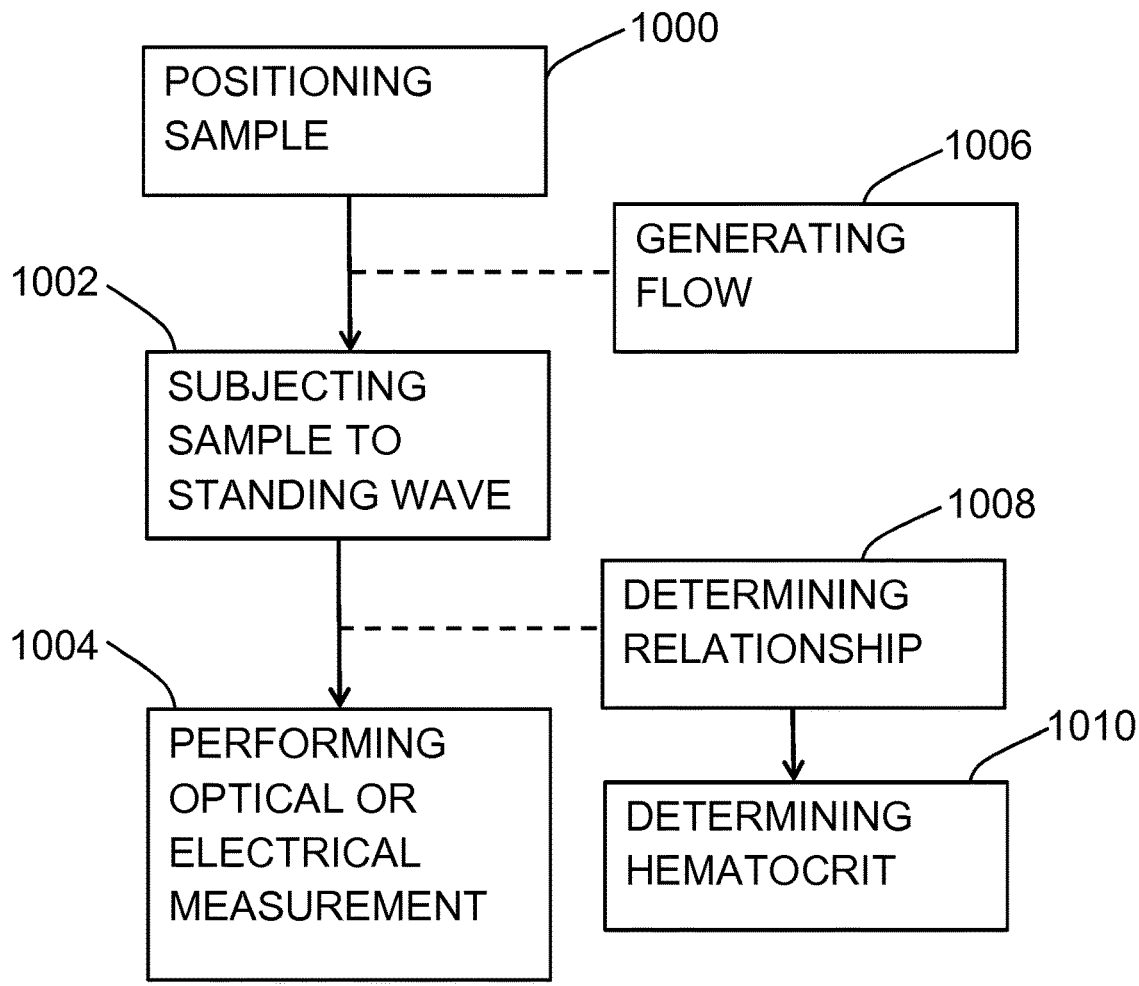

FIGS. 1A and B is a schematic view from above of a first embodiment of the method and system according to the first and second aspect of the present invention. FIG. 1A shows a silicon substrate 10 which has formed in it a microfluidic channel 12, defining a cavity, having an inlet 14, a central outlet 16, and two side outlets 18 and 20. An ultrasound transducer 22 is attached to the underside of the substrate 10, and the channel is delimited vertically by a glass sheet 24 bonded to the top of the substrate 10. The ultrasound transducer 22 may also be attached to the side of the substrate 10. A sample of whole blood 2 is admitted into the channel 12 through inlet 14, i.e. positioned as designated by step 1000 in FIG. 1B, and caused to flow towards the outlets 16, 18, and 20, i.e. by generating flow as designated by optional step 1006 in FIG. 1B. The ultrasound transducer 22 is activated with a frequency which varies from a frequency below the transversal resonance frequency of the channel 12 to a frequency above the resonance frequency. This gives rise to an acoustic standing wave, represented by 26, corresponding to step 1002 in FIG. 1B of subjecting the sample to a standing wave, which causes red blood cells, one of which is designated the reference numeral 4, representing particles, in the whole blood 2 to congregate in the pressure central node of the acoustic standing wave thus causing the red blood cells 4 to congregate in a first region, corresponding to the center portion, of the channel 12. As the whole blood 2 then passes the ultrasound transducer 22 the center portion of the flow, including the red blood cells 4, exit through the central outlet 16, whereas the remainder of the blood, i.e. the plasma 6, exits through the side outlets 18 and 20. An optical or electrical measurement, in particular an absorbance measurement can now be performed, as indicated by step 1004 in FIG. 1B, near the side outlet 18 at the area designated by the circle 28 in order to, for example, determine the concentration of hemoglobin, and thereby determine the percentage of the red blood cells 4 that have lysed, i.e. the degree of hemolysis in the sample of whole blood.

As will become evident from studying FIG. 1 the efficiency of congregating the red blood cells 4 into the center portion of the channel 12 is of paramount importance if the plasma 6 flowing through the side outlet 18 is to be clear from red blood cells 4 as even a very low concentration of red blood cells will prevent the absorbance measurement. Thus, where the ultrasound transducer 22 is driven at a single frequency which fails to correspond to a resonance frequency of the channel 12, for example because the substrate 10 and the channel 12 have been manufactured with wide tolerances or from a material, such as a polymer material, which does not allow narrow tolerances, then the efficiency of congregating the red blood cells 4 into the central outlet 16 will be low and the absorbance measurement will be hindered. This also applies when different samples 2 are used as the resonance frequency in the channel 12 is dependent also on speed of sound in the sample and on other factors such as temperature and length of the channel 12.

Although in FIG. 1 absorbance measurements are made in a sample of whole blood, other dispersive fluids may be similarly processed to make optical or electrical measurements in the regions of the fluid which the particles do not occupy after being forced to congregate into other regions.

Figure 2A:
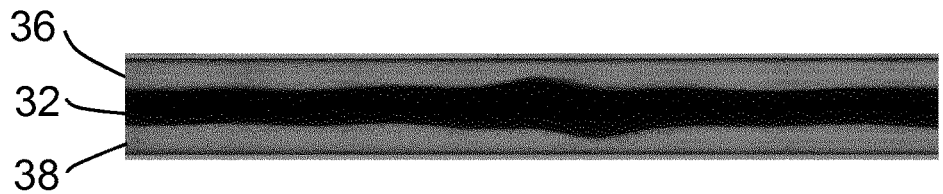
Figure 2B:
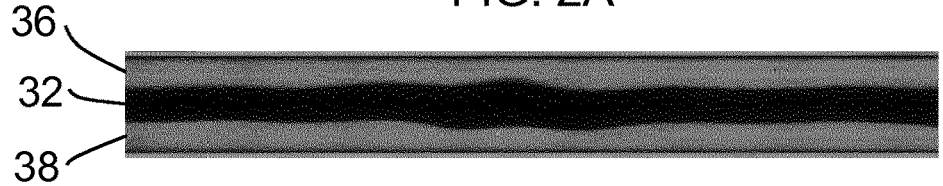

In addition, in certain embodiments of the method according to the first aspect of the present invention where the sample is whole blood the relationship between the volume of the red blood cells in the at least one first regions 32, see FIG. 2A, and the volume of the blood plasma in the at least one second regions 36, 38 in FIG. 2A is determined as specified in step 1008 by measuring the volume of the at least one first regions 32 and the volume of the at least one second regions 36, 38 where after the hematocrit may be determined as indicated by step 1010.

FIG. 2 is photographs showing the congregation of red blood cells with and without varying the frequency of the acoustic standing wave and taken at different times. Thus FIGS. 2A and 2B show the same section of a channel when a standing wave of a single frequency is used. The red blood cells congregate in the center of the channel, i.e. the first region 32 and the plasma occupy the second regions 36 and 38 flanking the center of the channel. Firstly it should be noted that the first region 32 is not of uniform cross section, rather the width of this region varies along the channel. Second, as is seen when comparing FIG. 2A to FIG. 2B, the first regions is not uniform over time because in FIG. 2B, which is taken about 5 seconds later, the broadened portion of the first regions 32 has moved to the left. Clearly it would be difficult to select an area of the second regions 36 and 38 where it would always be possible to perform the optical measurement as there is a risk that the red blood cells in the first regions 32 may obscure the selected area.

Figure 2C:
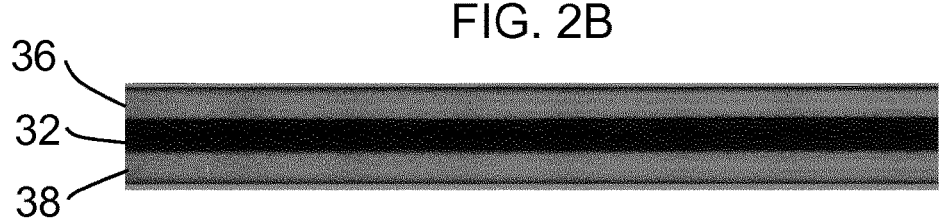
Figure 2D:
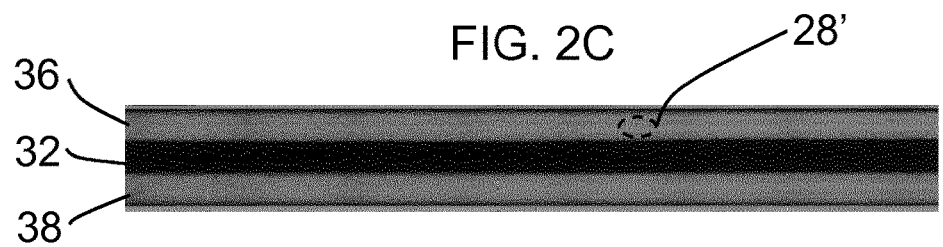

FIGS. 2C and 2D show the same section of the channel, however this time the frequency is varied, i.e. swept, between a frequency below the resonance frequency for a standing wave in the width dimension of the channel and a frequency above this frequency. As is shown when comparing FIGS. 2C and 2D the first region is uniform both spatially, i.e. along the channel, and temporally (the photographs are taken about 0.8 seconds apart). Thus in this case an area of the second regions can be selected as shown by the dashed circle 28'.

Accordingly, varying the frequency of the acoustic standing wave produces a more uniform congregation of the red blood cells both spatially and temporally, thus causing the reliable formation of at least one second region free of red blood cells/particles, through which an optical or electrical measurement, such as absorbance or transmission measurement of the amount or concentration of free hemoglobin, can be made.

The frequency may for example be swept between 1850 kHz and 2050 kHz. Transmitted light may be measured to measuring free hemoglobin at 420 nm.

FIG. 3 is a schematic view from above of a second embodiment of the method according to the first aspect of the present invention. FIG. 3 shows an elongated glass substrate 10' having formed within it a channel 12' 2 mm wide and 200 µm high. An inlet 14' to the channel 12' is provided at one end of the substrate 10' and an opposing outlet 16' is provided at the other end. Substrate 10' thus resembles a glass capillary. An ultrasound transducer 22' is coupled to the substrate 10' through a glass sheet 30, which glass sheet works as a coupling member for transferring the acoustic energy from the ultrasound transducer 22' to the substrate 10'. The use of the glass sheet 30 makes it easier to perform absorbance measurements in the channel 12' as the ultrasound transducer is no longer attached to the substrate below the channel. In FIG. 3 the transducer 22' is driven with a frequency varying around a higher multiple of the lowest resonance frequency of the channel 12', which produces the acoustic standing wave indicated by 26', which acoustic standing wave has two pressure nodes. Accordingly, when a sample of whole blood 2 has been introduced into the channel 12' the red blood cells will, at least in the vicinity of the acoustic standing wave 26', congregate into two bands in the first regions 32' and 34', one for each pressure node, leaving the plasma 6, i.e. the fluid, to occupy the remaining three second regions 36', 38' and 40'. It is thus possible to perform the optical or electrical measurement in one of these second regions.

FIG. 4 is a schematic part cross sectional view of a first embodiment of a system according to the second aspect of the present invention. FIG. 4A shows a system comprising, on one hand, a substrate 10" with channel 12" with inlet 14" and outlet 16", and on the other hand a housing 50 having a receptacle or opening 52 for receiving at least part of the substrate 10" and abutments 54, 56, 58 and 60 for positioning the substrate 10". The housing 50 further houses an ultrasound transducer 22" with a glass sheet 30' acting as a coupling member for transferring ultrasound energy to the substrate 10" when the substrate is received in the receptacle 52. A light source 62 is positioned beneath the glass sheet 30' in a predetermined position relative to the receptacle 52 and the abutments 54, 56, 58, 60 and a sensor 64 is positioned above, see FIG. 3B, to receive the light from the light source 62 through the substrate 10", the light source 62 and the sensor 64 representing a detector. A source of electrical power 66, such as a battery, as well as a control circuit 68 and a drive circuit 70 for the ultrasound transducer 22" are also contained within the housing 50.

In use a sample of a disperse fluid, e.g. blood, is allowed to flow into the channel 12" through the first inlet 14". The substrate 10" is then inserted into the receptacle 52 whereby the abutments 54, 56, 58 and 60 contact the substrate 10" to position it in a predetermined position. The control circuit 68 then controls the drive circuit 70 to energize the ultrasound transducer 22". In this position the substrate 10" is in contact with the glass sheet 30' so that ultrasound energy can be transferred into it to cause the particles in the disperse fluid, in this case red blood cells, to congregate in at least one first region of the channel 12". The position and dimension of the channel 12" relative to the substrate, and the position of the light source 62 and sensor 64, are so arranged that a second region devoid of red blood cells will always form so that an absorbance measurement can be performed. This is because the drive circuit 70 is configured to drive the ultrasound transducer 22" with a frequency that varies around a resonance frequency of the channel, thus even where there might be variances in the width of the channel 12" due to the manufacturing of the substrate 10", the red blood cells 4 will properly congregate leaving a second region devoid of red blood cells for the absorbance measurement. The control circuit 68 receives the result of the absorbance measurement from the sensor 64 and may directly, or after converting the result of the absorbance measurement (the result being in the form of a transmission value) into a degree of hemolysis value using a look up table or function derived from measurements of samples with known degrees of hemolysis display the result or the hemolysis level on a display (not shown) provided on the housing, or may store the result or the hemolysis level within the control circuit 68 for later retrieval.

Third and Fourth Aspects of the Present Invention

As shown from the above discussion and disclosure, varying the frequency of the acoustic standing wave in a microfluidic cavity is advantageous. The present inventors have found that these advantageous may be employed also for other measurements.

Accordingly, third and fourth corresponding aspects of the present invention concern a method and system for determining hematocrit in whole blood.

Hematocrit (HCT) is the volume fraction of red blood cells in blood, which is an important indicator of a patient's blood status. Measurement of the HCT is useful for the diagnosis of several diseases and conditions, such as anemia, polycythemia, dehydration and blood loss due to bleeding. Traditionally, the microhematocrit method has been used to measure HCT. In this method, a blood filled capillary is centrifuged and the relative height of the packed cell fraction is measured, also known as the packed cell volume (PCV). The microhematocrit method has been replaced in most modern hospitals (often with centralized lab facilities) by whole blood analyzers, which are instruments based on electrical impedance measurements (the coulter principle). However, the microhematocrit method is still employed at smaller hospitals and at the doctor's office due to the lower cost and simple readout.

Microfluidics has been suggested for HCT determination, however with accuracies no better than 2.6% HCT and sample to answer times of 5 minutes, there is still a need for faster and more accurate measurements of HCT.

Accordingly it is an additional object of the present invention to provide a fast and/or more accurate method and system for determining hematocrit in whole blood.

It is a further additional object of the present invention to provide a method and system for determining hematocrit in whole blood which can be automated and/or which does not require further chemicals.

At least one of these objects, or at least one of the further objects which will become evident from the below description, are according corresponding third and fourth aspects of the present invention achieved by a method of measuring hematocrit of a blood sample, the blood sample comprising at least red blood cells and at least blood plasma, the method comprising the steps of:

a) positioning the blood sample in a microfluidic cavity having a resonance frequency, b) subjecting the blood sample, in the cavity, to an acoustic standing wave configured for causing the red blood cells to congregate in at least one first region of the cavity, thereby causing the blood plasma to occupy at least one second region of the cavity, wherein the frequency of the acoustic standing wave is varied between a frequency below the resonance frequency and a frequency above the resonance frequency, and c) determining a relationship between the volume of the red blood cells in the at least one first region and the volume of the blood plasma in the at least one second region, and d) determining the hematocrit of the blood sample based on the relationship, and a microfluidic system for measuring hematocrit of a blood sample, the blood sample comprising at least red blood cells and at least blood plasma, the system comprising a substrate with a microfluidic cavity formed in the substrate, the microfluidic cavity having an inlet for allowing the blood sample into the microfluidic cavity, an ultrasound transducer connected to the substrate for generating an acoustic standing wave in the microfluidic cavity, a drive circuit operationally connected to the ultrasound transducer and configured to drive the ultrasound transducer with a frequency which is varied between a frequency below a resonance frequency of the microfluidic cavity and a frequency above the resonance frequency so as to cause the red blood cells to congregate in at least one first region of the cavity, thereby causing the blood plasma to occupy at least one second region of the cavity, a detector arranged or configured to determine a relationship between the volume of the red blood cells in the at least one first region and the volume of the blood plasma in the at least one second region, and a computer for determining the hematocrit of the blood sample based on the relationship.

The blood sample may be a diluted or undiluted whole blood sample.

The blood sample may be positioned in the cavity by pumping, by pressure, by suction, by the action of electrical fields, by gravity, and by capillary action.

The microfluidic cavity may be closed to the environment. The microfluidic cavity is preferably a channel having a square or rectangular cross section. The microfluidic cavity may for example have a cross sectional width of 1 to 20 times the cross sectional height. In this case the length of the microfluidic cavity is at least the same as the width. The width may for example be from 0.3 mm to 5 mm. The height may for example be from 0.025 mm to 1 mm.

Resonance frequencies of the microfluidic cavity are dependent on the dimensions because, in order for a standing wave to form the wavelength λ of the wave, which wavelength is inversely proportional to the frequency, must be nλ/2 where n is a positive integer.

The following are the first 3 resonances for a standing wave directed along the width dimension of the cavity:

a first resonance frequency f is associated with an acoustic standing wave λ/2 corresponding to a first harmonics w here the pressure anti nodes of the standing wave are positioned near the walls of the cavity and a single pressure node is formed in the middle of the cavity, thus causing the particles to congregate in the center of the cavity, this being the first region and the regions near the side walls of the cavity being the second regions. Thus we get: wall 1-fluid 1-particles 1-fluid 2-wall 2.

In a second harmonics, corresponding to a resonance frequency that is two times the first resonance frequency, i.e. 2f, a standing wave λ is formed having two nodes and three antinodes, thus generally forcing the particles to congregate in two bands on both sides of the center of the cavity, this being the first regions and the center and sides of the cavity being the second regions. Thus we get: wall 1-fluid 1-particles 1-fluid 2-particles 2-fluid 3-wall 2. This is the preferred resonance frequency.

A third resonance frequency, corresponding to a third harmonics, is three times the first resonance frequency, i.e. 3f, and is associated with a standing wave 3λ/2 having 3 nodes and four antinodes, thus forcing the particles to congregate in three positions in the cavity, these three being the first regions, these positions being spaced apart from each other and from the walls of the cavity to form three second regions. Thus we get: wall 1-fluid 1-particles 1-fluid 2-particles 2-fluid 3-particles 3-fluid 4-wall 2.

Accordingly the term resonance frequency is to be understood to comprise any frequency in which a standing wave may form in the cavity, and a frequency causing the formation of a standing wave is considered a frequency configured for causing the particles to congregate in at least one first region. Additionally it should be mentioned that even if the resonance, and thus the standing wave, is predominantly in a width dimensions, there will always be components of resonance along the length dimension of the cavity and potentially also in the height direction. These three-dimensional resonances result in several resonance frequencies close to the one-dimensional resonance frequency, each with an associated focusing pattern. Sweeping the actuation frequency over several of these resonance frequencies makes it possible to take advantage of all of them and create a more predictable and even acoustic focusing, generated by the resulting weighted average of the acoustic fields for the separate resonances and thus combined focusing patterns.

The understanding that the acoustic resonances have to be understood in three dimensions and not only simplified to one dimension thus generates practically crucial effects, by generating a predictable, repeatable and robust acoustic focusing pattern. This in turn enables detection at predictable, repeatable positions in the system, not possible with single frequency actuation.

The resonance frequency of the cavity, and thus the frequency of the acoustic standing wave, may thus be from 0.15 Mhz to 10 MHz.

The frequency may be varied from a frequency 20% below the resonance frequency to a frequency 20% above the resonance frequency. Preferably the frequency is varied from a frequency 10% below the resonance frequency to a frequency 10% above the resonance frequency. The frequency may be varied continuously, or alternatively only during some time, during the time that the sample/disperse fluid is subjected to the acoustic standing wave. The frequency may be varied linearly, or logarithmically.

The frequency should not be varied from a frequency that is so low, or to a frequency that is so high, that the frequency corresponds to a different resonance frequency of the cavity that will lead to a different number of nodes and antinodes than what is obtained at the resonance frequency.

In other words the frequency $f_{DN}$, for causing the particles to congregate in at least one first region of a cavity having some dimension D corresponding to N half wavelengths of the acoustic standing wave corresponding to $f_{DN}$, should, when varied according the aspects of the present invention, always be higher than $(c*(N-1))/(2*D)$ and lower than $(c*(N+1))/(2D)$, where c is the speed of sound in the fluid.

In practice a sweep range of 1% to 40% of $f_{DN}$, i.e. the frequency being varied over the range of ±0.5-20% of $f_{DN}$, is sufficient to cover the resonance frequencies corresponding to a certain number of pressure nodes as well as the fabrication tolerances of the channel and the variation in sample speed of sound.

The actuation signal for the ultrasound transducer may preferably be a linearly chirped sine with a repetition rate of 1000 Hz, and amplitude of approximately 15 Vpp (Voltage peak-peak).

In other words the actuation signal for the ultrasound transducer may for example be a linearly chirped sine with a sweep time of 1 ms. The amplitude for the signal may be 15 Vpp (Voltage peak-peak)

The sweep time should be much shorter than the time frame during which congregation occurs. Thus the repetition rate should be high enough so that the sweep time is much shorter than the time frame during which congregation occurs. As an example, when the particles are congregated in the cavity over a time frame of 5 seconds the repetition rate of the sweep can be set such that the frequencies are cycled through 100 times or more, i.e. at least 20 repetitions per second, corresponding to a sweep time of 50 ms or less. Thus the sweep time may for example be 100 ns-50 ms, such as 1-50 ms.

Too slow sweep time leads to the shape of the first and second regions changing during the measurement time, i.e. the time that the sample is subjected to the acoustic standing wave.

The relationship may for example be a ratio or percentage of the volume or area of the red blood cells.

The relationship may for example be determined using a detector such as a camera or a light sensitive sensor array. A light source may be provided on the opposite side of the cavity from the camera or light sensitive array. The relationship may be determined by thresholding an image of at least part of the cavity and assigning counting the number of pixels having a value below the threshold vs the total number of pixels.

The volume of the red blood cells in the at least one first regions and the volume of the blood plasma in the at least one second regions need not be calculated provided that the cavity is of uniform dimensions where the determining of the relationship is performed.

Thus the relationship of the volumes may be determined by measuring the area of the at least one first region and the area of the at least one second region the area being determined in a plane made up of two orthogonal dimensions (XY) of the cavity provided that the regions have the same extension in the third dimension (Z) of the cavity, or that the measurement is adjusted for the variation in depth in the Z direction.

The combined volume of all first regions and the combined volume of all second regions may be measured for determining the relationship.

The hematocrit may be determined from the relationship by using the method on samples of known hematocrit and determining the relations ships for these samples to prepare a correlation between hematocrit values and the relationship.

The computer is preferably further arranged and programmed for first actuating the drive circuit and then actuate the detector.

The method and system according to the third and fourth aspects of the present invention could also be used to determine the volume fraction of particles in other disperse fluids such as intracellular fluid, interstitial fluid, synovial fluid, peritoneal fluid, urine, yeast cell cultures, bone marrow and stroma.

In the preferred embodiment of the method according to the third aspect of the present invention the blood sample is subjected to the acoustic standing wave for 20 seconds or less such as 5 seconds or 2 seconds before the step of determining the relationship between the volume of the red blood cells in the at least one first region and the volume of the blood plasma in the at least one second region is performed.

Correspondingly the detector and/or computer may be arranged or configured to determine the relationship between the volume of the red blood cells in the at least one first region and the volume of the blood plasma in the at least one second region after the blood sample is subjected to the acoustic standing wave for 20 seconds or less, such as 5 seconds or 2 seconds.

The detector may be configured to determine the relationship by being configured to obtain the reading or the image at these times, or by providing the computer with an image or reading at these times.

The detector may be configured to determine the relationship being programmed or configured to obtain, from the detector, an image or reading at these times.

Additionally the drive circuit may be configured to provide the acoustic standing wave for these times.

In the preferred embodiment of the method and system according to the corresponding third and fourth aspect of the present invention the cavity is formed in a substrate. The substrate may be made of silicon but may be made of polymeric material such as plastic, or alternatively glass. Also other materials such as ceramics and metals are possible. These materials are cheap and therefore suitable for performing the optical or electrical measurements in the field on in a point of care setting, as disposable consumables.

The method and system according to the third and fourth aspects of the present invention will now be further described with reference to FIGS. 5-9.

FIGS. 5A and B are a schematic view of an embodiment of the method according to the third aspect of the present invention being performed using a first embodiment of the system according to the fourth aspect of the present invention. Thus FIG. 5A shows a system 100 comprising a glass substrate 110 with a channel 112 having an inlet 114 and an outlet 116. An ultrasound transducer 122 is connected to the substrate 110, for example by being glued to it, for subjecting the sample to a standing wave as designated by step 1022 in FIG. 5B. A light source 162 is positioned under the channel 112 and a camera 164 is arranged so as to be able to obtain a transmission image of the channel 112 according to the outline 172, e.g. for determining the relationship between the volume of the red blood cells in the at least one first regions and the volume of the blood plasma in the at least one second regions by measuring the volume of the at least one first regions and the volume of the at least one second regions as designated by the step 1024 in FIG. 5B, and is connected to a computer 168 for determining the hematocrit based on this relationship as designated by the step 1026 in FIG. 5B. The computer 168 is further connected to control a function generator 170 which is configured to actuate the ultrasound transducer with a frequency that varies from below a resonance frequency of width dimension of the channel 112 to a frequency above this resonance frequency. A blood sample 102 is aspirated by a syringe 176 through the channel 112, i.e. positioned in the cavity as designated by step 1020 in FIG. 5B, and two tree-way valves 178 and 180 are provided for routing the blood sample through the channel 112, or for alternatively routing a cleaning solution through the channel 112 between samples. A bypass channel 182 is also provided between the valves 178 and 180.

For evaluating the system 100, the following experimental specifications were used:

The microfluidic channel 112 was manufactured by Micronit Microfluidics (Enschede, Netherlands) and was fabricated in borosilicate glass substrate 110 using photolithography and isotropic wet etching. The microfluidic channel was 400 µm wide and 150 µm deep. Fluidic access was enabled by sandblasting holes in the ends of the channel, and silicone tubing was attached over the holes using silicone glue (Elastosil A07, Wacker Elastics) to provide fluidic ports 114, 116. The ultrasound transducer 122 was a piezoceramic transducer (Ferroperm AS, Denmark) which was glued to the chip/substrate 110 using cyanoacrylate glue (Loctite).

Blood samples 102 were obtained from healthy donors after informed consent from all participants. For obtaining a standard series, different HCT levels were obtained by adding of either autologous plasma or blood cells to the donor sample. Experimentally, whole blood from a single healthy donor was split into two parts. One part was centrifuged (2000×g for 10 min) to generate separated blood plasma and blood cells, which in turn were mixed in defined portions with the un-centrifuged donor blood to obtain samples with the hematocrit levels used in the study.

Reference measurements of all samples were made using a hematocrit centrifuge (Hematokrit 210, Hettich GMBH, Germany) according to the manufacturer's protocol. A blood filled capillary was centrifuged at 130 k rpm for 2 min, and the PCV value was manually read from a scale bar with 1 percentage point (p.p) increments and rounded to the closest integer value, which yielded a rounding error of +−0.5 p.p. Each sample was measured three times, and the precision of the method was within the rounding error.

A 200 μL sample was aspirated from a 1.5 ml Eppendorf tube into the microfluidic channel 112 using a syringe pump 176 (NeMESYS, Cetoni GMBH, Germany). The flow was stopped by short-circuiting the inlet and outlet using two two-position three-way valves 178, 180 (NeMESYS).

The piezoceramic transducer 122 was actuated by an amplified signal (AR 75A250, Amplifier Research, Souderton, Pa., USA) generated by a function generator 170 (Tectronix AFG3022B). The actuation signal was a linearly chirped sine ranging from 1.8-2.1 MHz with a duty cycle of 1 msec, and peak-to-peak amplitude of approximately 15 V. In-house developed LabVIEW software controlled the function generator.

The microfluidic channel 112 was imaged using a microscope (DM2500 M, Leica Microsystems CMS GmbH, Germany) with an 8-bit grayscale CCD camera 164 (EoSens mini MC-1370, Mikrotron GmbH, Unterschleissheim, Germany). A white LED array used as light source 162 and placed under the chip/substrate 110 for transmission imaging. A segment of approximately 3.5 mm by 0.6 mm of the microfluidic channel 112 was imaged. The image acquisition at 20 Hz was hardware triggered upon activation of the ultrasonic actuation.

The Acoustically Packed Cell Volume, APCV, was measured from the acquired images using a basic image analysis algorithm implemented in MatLab. Briefly, the red blood cells absorb strongly in transmission mode microscopy, and are represented as dark pixels in the images. The blood plasma is transparent and is represented as bright pixels. The image was cropped along the channel walls using boundaries initially set by the user, and converted to 1-bit binary through thresholding using a threshold level at 30% of maximum pixel value. This threshold value was initially chosen as it generated a similar result to what the user perceived as the blood-plasma boundary in the unprocessed image. The image was inverted, and the APCV value was calculated as the number of bright pixels (sum of the binary image), divided by the total number of pixels in the image (image size).

FIG. 6 shows photographs of the microfluidic cavity and subsequent thresholding techniques to determine the area occupied by red blood cells vs the area occupied by blood plasma. Thus panel A of FIG. 6 shows the whole blood-filled microfluidic channel prior to subjecting the blood sample to the acoustic standing wave, the dashed lines showing the walls of the channel. Panel B shows whole blood (40% PCV) being focused to the center of the channel after 20 s of ultrasonic actuation. The acoustic standing wave is indicated by the hourglass shaped dashed lines. Panel C shows the inverted threshold image used for the APCV measurement.

When performing the experiment and obtaining the photographs in FIG. 6 the effect of using the linear frequency sweep for the actuation of the ultrasound transducer 122 was clearly noticeable. First, it averaged out resonances directed along the channel length and reduced the presence of acoustic "hot spots" that the acoustic field became invariant along the channel. Second, the chirped signal eliminated the need for sample specific tuning of the actuation frequency. As the speed of sound in blood depends on the hematocrit level an operator would otherwise have to tune the actuation frequency to match the required A condition.

FIG. 7 is a graph showing the correlation between the Acoustically Packed Cell Volume (APCV) and the Packed Cell Volume (PCV). This graph was obtained in order to test the linearity of the measurement method. A dilution standard series of blood samples with different hematocrit levels was prepared. The standard series contained a total of 17 blood samples with HCT ranging from 20% to 60%, in 2.5 percentage points (p.p) increments. The HCT of each sample was measured 3 times with the method according to the third aspect of the present invention, and 3 times by centrifugation as control. The centrifugation measurement had a resolution of 1p.p.

The APCV values of the samples in the standard series were measured after 20 s of acoustic actuation and showed a linear correlation to the PCV values. A linear regression (y=0.986x+4.12) yields an R2 value of 0.987. For residuals, see SI.2. The whole measurement process of a single sample, including sample loading, acoustic packing of the cells, image analysis and washing of the channel could be performed in less than 60 s.

FIG. 8 shows the temporal evolution of the relationship between the area occupied by red blood cells vs the area occupied by blood plasma. Thus it was found that while the optical readout was preferably performed after 20 s of acoustic actuation to make sure the obtained signal had reached steady state, the measured value reached a plateau after approximately 5 s. We furthermore observed an increased time to reach steady state for blood with higher PCV, see panel A. Panels B-E show photographs of the channel at different time points.

Further test were made to assess the accuracy of the method and system. Thus the APCV values of blood samples from one male (Y1) and 4 female (X1-4) healthy donors were measured. For comparison, we used the linear relationship between APCV and PCV values obtained from the standard series, see FIG. 7, to calculate the PCV equivalent of the APCV value, denoted as the PCVE, the results being provided in the table below:

| Sample | Mean APCV (%) | Mean PCVE (%) | PCVE standard deviation (p.p) | Mean PCV (reference) | Mean error (p.p) |
| --- | --- | --- | --- | --- | --- |
| X1 | 46.28 | 42.7 | 0.99 | 43% | −0.27 |
| X2 | 44.89 | 41.3 | 0.99 | 42% | −0.68 |
| X3 | 44.34 | 40.8 | 0.67 | 43% | −2.24 |
| X4 | 46.65 | 43.1 | 0.96 | 44% | −0.90 |
| Y1 | 51.18 | 47.7 | 0.66 | 48% | −0.64 |

Each sample was measured three times (n=3). The measurement error for each sample (calculated as the mean PCVE-mean PCV) was <1 p.p for all samples except sample X3, where our method on average underestimated the PCV of the sample by 2.24 p.p. The standard deviation of three measurements was below 1 p.p for all samples. As an indicator of the system accuracy, the average absolute error was calculated to be 1.13 p.p, and the average error was 0.95 p.p.

FIG. 9 is a graph showing the correlation between APCV and PCV obtained at different time points. Thus this graph shows that an accurate prediction of the PCV equivalent can be performed already after 2 s of acoustic actuation. As a comparison to the 20 second APCV standard series APCV in FIG. 7, APCV values were also derived after 2 and 5 s of acoustic actuation, displaying a linear correlation with the PCV, see FIG. 9. The table below shows the linear parameters for the three time points of APCV readout:

| Time | Linear fit eq. | $R^2$ value |
|---|---|---|
| 20 seconds | y = 0.9867x − 0.0412 | 0.9861 |
| 5 seconds | y = 1.0544x − 0.0369 | 0.9884 |
| 2 seconds | y = 1.1899x − 0.0253 | 0.9887 |

All three APCV time points displayed a linear performance that enables accurate HCT estimation. However, estimating APCV in the very early phase of acoustic focusing makes the measurement procedure more sensitive to system variations, i.e. deviations in acoustic energy and timing of data collection. By collecting data in the early phase of focusing the time derivative of the temporal APCV curve is large and hence any variation in either acoustic energy or timing will have a larger impact on readout than in the low derivative region where the cells are closely packed. Estimating APCV for the five clinical samples at time point 2 and 5 seconds gives slightly higher PCVE, although within an error margin of approximately 1%, see the below table.

| | 5 seconds | | | 2 seconds | | | |
|---|---|---|---|---|---|---|---|
| Sample | Mean PCVE | Std. dev. (p. p.) | Mean error (p. p.) | Mean PCVE | Std. dev. (p. p.) | Mean error (p. p.) | PCV (ref) |
| X1 | 44.5% | 1.83 | 1.15 | 45.1% | 2.06 | 2.1 | 43% |
| X2 | 42.3% | 1.72 | 0.34 | 42.7% | 1.98 | 0.74 | 42% |
| X3 | 41.8% | 0.84 | −1.18 | 42.5% | 1.41 | −0.46 | 43% |
| X4 | 44.7% | 1.36 | 0.69 | 45.1% | 1.16 | 1.16 | 44% |
| Y1 | 49.6% | 1.11 | 1.25 | 49.7% | 1.08 | 1.40 | 48.3% |

Feasible Modifications of the Invention

The invention is not limited only to the embodiments described above and shown in the drawings, which primarily have an illustrative and exemplifying purpose. This patent application is intended to cover all adjustments and variants of the preferred embodiments described herein, thus the present invention is defined by the wording of the appended claims and the equivalents thereof. Thus, the equipment may be modified in all kinds of ways within the scope of the appended claims.

For instance, it shall be pointed out that structural aspects of embodiments of the method according to the first aspect of the present invention shall be considered to be applicable to embodiments of the system according to the second aspect of the present invention, and conversely, methodical aspects of embodiments of the system according to the second aspect of the present invention shall be considered to be applicable to embodiments of the method according to the first aspect of the present invention.

It shall also be pointed out that all information about/concerning terms such as above, under, upper, lower, etc., shall be interpreted/read having the equipment oriented according to the figures, having the drawings oriented such that the references can be properly read. Thus, such terms only indicates mutual relations in the shown embodiments, which relations may be changed if the inventive equipment is provided with another structure/design.

It shall also be pointed out that even thus it is not explicitly stated that features from a specific embodiment may be combined with features from another embodiment, the combination shall be considered obvious, if the combination is possible.

Throughout this specification and the claims which follows, unless the context requires otherwise, the word "comprise", and variations such as "comprises" or "comprising", will be understood to imply the inclusion of a stated integer or steps or group of integers or steps but not the exclusion of any other integer or step or group of integers or steps.

The invention claimed is:

1. A method of performing an optical or electrical measurement in a sample (2) of a disperse fluid, the sample comprising particles (4) and a fluid (6), comprising the steps of:
   a) positioning (1000) the sample (2) in a microfluidic cavity (12) having a resonance frequency,
   b) subjecting (1002) the sample (2), in the cavity (12), to an acoustic standing wave configured for causing the particles (4) to congregate in at least one first region (32) of the cavity, thereby causing the fluid (6) to occupy at least one second region (36, 38) of the cavity (12), wherein the frequency of the acoustic standing wave is repeatedly varied between a frequency below the resonance frequency and a frequency above the resonance frequency, and
   c) performing (1004) an optical or electrical measurement in the fluid in at least one of the at least one second region of the cavity.

2. The method according to claim 1, wherein the acoustic standing wave is configured for causing the particles (4) to congregate in one or two first regions (32', 34') of the cavity (12).

3. The method according to claim 1, further comprising the step of:
   d) generating (1006) a flow of the sample (2) through the cavity (12).

4. The method according to claim 3, wherein the cavity (12) is elongated and fluidly connected at one end to an inlet (14) and at another opposite end to an outlet (16).

5. The method according to claim 1, wherein the cavity (12) is formed in a substrate (10).

6. The method according to claim 5, wherein ultrasound energy, for causing the acoustic standing wave, is transferred to the substrate (10) from at least one ultrasound transducer (22') solely via a glass coupling member (30) connected to the ultrasound transducer and the substrate.

7. The method according to claim 1, wherein the sample (2) is a blood sample whereby the particles comprises at least red blood cells (4) and the fluid comprises at least blood plasma (6).

8. The method according to claim 7, wherein the optical or electrical measurement is an absorbance measurement comprising determining the amount or concentration of free hemoglobin in the blood plasma (6).

9. The method according to claim 7, wherein the method further comprises the steps of:
   d) determining (1008) a relationship between the volume of the red blood cells (4) in the at least one first region (32) and the volume of the blood plasma (6) in the at least one second region (36, 38) by measuring the volume of the at least one first region (32) and the volume of the at least one second region (36, 38), and e) determining (1010) the hematocrit of the blood sample based on the relationship.

10. A microfluidic system for performing an optical or electrical measurement in a sample (2) of a disperse fluid, the sample comprising particles (4) and a fluid (6), the system comprising
- a substrate (10) with a microfluidic cavity (12) formed in the substrate, the microfluidic cavity having an inlet (14) for allowing the sample into the microfluidic cavity,
- an ultrasound transducer (22") connected to the substrate for generating an acoustic standing wave in the microfluidic cavity,
- a drive circuit (70) operationally connected to the ultrasound transducer (22") and configured to drive the ultrasound transducer with a frequency which is repeatedly varied between a frequency below a resonance frequency of the microfluidic cavity and a frequency above the resonance frequency so as to cause the particles to congregate in at least one first region (32) of the cavity, thereby causing the fluid to occupy at least one second region (36, 38) of the cavity, and
- a detector (64) arranged for performing an optical or electrical measurement in the fluid in at least one of the at least one second region of the cavity.

11. The microfluidic system according to claim 10, further comprising
- a housing (50) comprising a receptacle (52) arranged to receive at least part of the substrate (10"),
- wherein the ultrasound transducer (22") is provided in the housing and is arranged to connect to the substrate when the substrate is received in the receptacle, and
- wherein the detector (64) is provided in the housing and is arranged in a predetermined position relative to the substrate when the substrate is received in the receptacle,
  - the predetermined position being arranged for allowing the detector to perform the optical or electrical measurement in the at least one of the at least one second region (36, 38) of the cavity (12".

12. The system according to claim 10, further comprising a glass coupling member (30') attached to the ultrasound transducer (22") for connecting the ultrasound transducer to the substrate (10").

13. The system according to claim 10, wherein the detector is further arranged for determining a relationship between the volume of the particles (4) in the at least one first regions (32, 34) and the volume of the fluid (6) in the at least one second regions (36 38), by being configured to measure the volume of the at least one first region (32) and the volume of the at least one second region (36, 38).

14. A method of measuring hematocrit of a blood sample (2), the blood sample comprising at least red blood cells (4) and at least blood plasma (6), the method comprising the steps of:
- a) positioning (1020) the blood sample in a microfluidic cavity (10) having a resonance frequency,
- b) subjecting (1022) the blood sample, in the cavity, to an acoustic standing wave configured for causing the red blood cells to congregate in at least one first region (32) of the cavity, thereby causing the blood plasma to occupy at least one second region (36, 38) of the cavity,
  - wherein the frequency of the acoustic standing wave is repeatedly varied between a frequency below the resonance frequency and a frequency above the resonance frequency, and
- c) determining (1024) a relationship between the volume of the red blood cells in the at least one first region and the volume of the blood plasma in the at least one second region, and
- d) determining (1026) the hematocrit of the blood sample based on the relationship.

15. The method according to claim 14, wherein the blood sample (2) is subjected to the acoustic standing wave for 20 seconds or less, before the step of determining the relationship between the volume of the red blood cells (4) in the at least one first region (32) and the volume of the blood plasma (6) in the at least one second region (36, 38) is performed.

16. The method according to claim 14, wherein the relationship is determined using a camera or a light sensitive sensor array (64).

17. A microfluidic system (100) for measuring hematocrit of a blood sample (102), the blood sample comprising at least red blood cells (4) and at least blood plasma (6), the system comprising
- a substrate (110) with a microfluidic cavity (112) formed in the substrate, the microfluidic cavity having an inlet (114) for allowing the blood sample into the microfluidic cavity,
- an ultrasound transducer (122) connected to the substrate for generating an acoustic standing wave in the microfluidic cavity,
- a drive circuit (170) operationally connected to the ultrasound transducer and configured to drive the ultrasound transducer with a frequency which is repeatedly varied between a frequency below a resonance frequency of the microfluidic cavity and a frequency above the resonance frequency so as to cause the red blood cells (4) to congregate in at least one first region (32) of the cavity, thereby causing the blood plasma (6) to occupy at least one second region (36, 38) of the cavity,
- a detector (164) configured to determine a relationship between the volume of the red blood cells in the at least one first region and the volume of the blood plasma in the at least one second region, and
- a computer (168) programmed to determine the hematocrit of the blood sample based on the relationship.

18. The system (100) according to claim 17, wherein the detector (164) and/or computer (168) is configured to determine the relationship between the volume of the red blood cells (4) in the at least one first region (32) and the volume of the blood plasma (6) in the at least one second region (36) after the blood sample has been subjected to the acoustic standing wave for 20 seconds or less.

19. The system according to claim 17, wherein the detector (164) is a camera or a light sensitive sensor array.

20. The method according to claim 14 wherein the blood sample (2) is subjected to the acoustic standing wave for 5 or 2 seconds, before the step of determining the relationship between the volume of the red blood cells (4) in the at least one first region (32) and the volume of the blood plasma (6) in the at least one second region (36, 38) is performed.

* * * * *